United States Patent [19]

Meunier

[11] 4,110,581
[45] Aug. 29, 1978

[54] DEVICE FOR MONITORING THE FITTING IN POSITION OF DETACHABLE ELEMENTS IN THEIR SUPPORT

[75] Inventor: Jacques Meunier, Paris, France

[73] Assignee: C.G.R. MeV, Paris, France

[21] Appl. No.: 666,266

[22] Filed: Mar. 12, 1976

[30] Foreign Application Priority Data

Mar. 14, 1975 [FR] France .................... 75 08074

[51] Int. Cl.² .......................... H01H 3/42; H01H 3/16
[52] U.S. Cl. .................. 200/153 LA; 74/568 R; 200/153 L; 200/153 LB; 250/414; 250/510; 350/315
[58] Field of Search ......... 200/56 R, 153 LA, 153 L, 200/153 LB; 350/315; 250/414, 510; 74/568 R, 569

[56] References Cited

U.S. PATENT DOCUMENTS

| | | | |
|---|---|---|---|
| 1,989,803 | 2/1935 | Hoben | 200/153 LA |
| 2,462,302 | 2/1949 | Bolsey | 350/315 |
| 3,045,506 | 7/1962 | Glasgow | 74/568 R |
| 3,267,767 | 8/1966 | Neal | 200/153 L |
| 3,539,736 | 11/1970 | Naimer | 200/153 LA |
| 3,721,826 | 3/1973 | Thomas | 250/514 |
| 3,743,799 | 7/1973 | Cork et al. | 74/568 R |
| 3,854,049 | 12/1974 | Mistretta et al. | 250/510 |
| 4,018,151 | 4/1977 | Urban et al. | 74/568 R |

*Primary Examiner*—Edward A. Miller
*Attorney, Agent, or Firm*—Oblon, Fisher, Spivak, McClelland & Maier

[57] ABSTRACT

A device for detecting the absence or improper positioning of detachable elements in their supports comprises a system for monitoring the fitting in position of selected elements on a mounting plate provided at its periphery with slots, these slots being associated with obturating-studs. These studs are retractable from the corresponding slots when a corresponding detachable element is appropriately positioned in the mounting plate which is immobilized by means of a safety locking system comprising an index which can be introduced into this corresponding slot after the retraction of the obturating-stud from it, this index enabling to actuate a safety electrical switch.

10 Claims, 3 Drawing Figures

DEVICE FOR MONITORING THE FITTING IN POSITION OF DETACHABLE ELEMENTS IN THEIR SUPPORT

BACKGROUND OF THE INVENTION

1. Field of the Invention

Certain equipment using radiation beams, in particular radiotherapy apparatus, use detachable elements (filters or targets for example) arranged in the path of the radiation beam.

2. Description of the Prior Art

The absence or improper positioning of these detachable elements can seriously jeopardize patients being treated by such radiation beams.

SUMMARY OF THE INVENTION

The object of the present invention is to provide a device for mechanically monitoring the presence and proper positioning of these detachable elements in their mounting, prior to the commencement of operation of the irradiation apparatus.

In accordance with the invention, a device for monitoring the positioning of detachable elements in their mountings comprises a mounting plate with $n$ openings known as "locations", designed to receive the detachable elements, the mounting plate being provided at its periphery with a thick rim containing $n$ slots and a system for monitoring the positioning of the elements which comprises $n$ obturating-studs associated with $n$ slots; each of the studs being retractable from its slot when the detachable element is appropriately positioned in its corresponding location; the mounting plate being immobilizable in a given position by means of a safety locking system comprising an index which can be introduced into the slot corresponding to the selected location, after the retraction of the stud from the slot when the selected location is equipped with its detachable element; and means being provided for positioning the selected slot opposite the index and the index actuating an electrical switch.

BRIEF DESCRIPTION OF THE DRAWINGS

For a better understanding of the invention and to show how the same may be carried into effect, reference will be made to the drawings, given solely by way of example, which accompany the following description, and wherein.

DETAILED DESCRIPTION OF THE PREFERRED EMBODIMENTS

Figure 1:
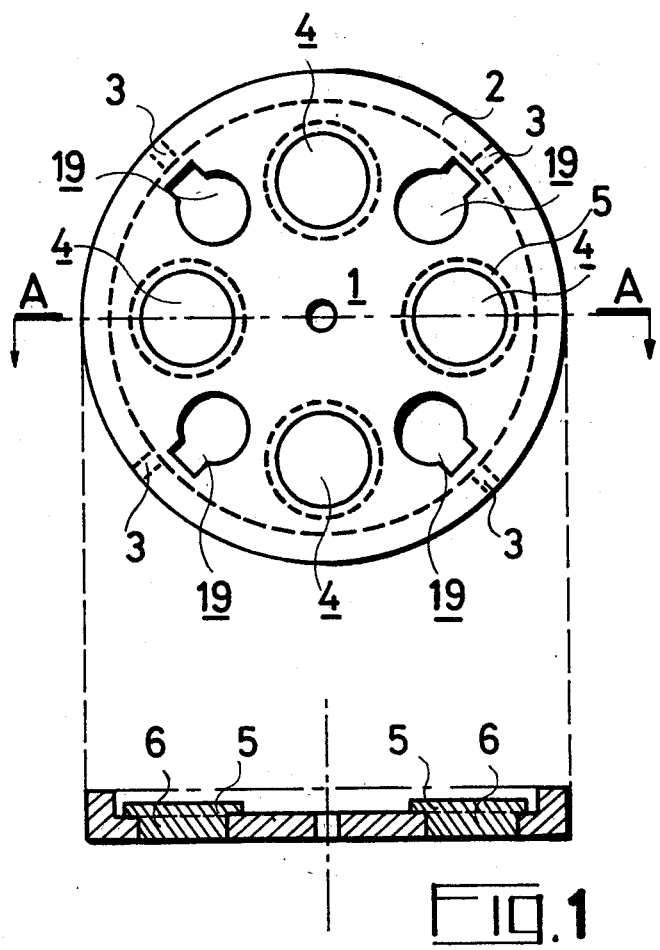
FIG. 1 illustrates a detail of a mounting plate belonging to the device in accordance with the invention.

The monitoring device in accordance with the invention comprises, in one embodiment shown in FIG. 1, a mounting plate 1 made, for example, of metal and having a circular shape, exhibiting at its periphery a thick rim 2 provided with $n$ slots 3 of cylindrical shape with their axes parallel to the mounting plate 1. The mounting plate 1 is provided, in the peripheral zone, with $n$ openings 4 known as "locations", in which there can be respectively disposed $n$ detachable elements 6, each having a supporting collar 5.

Figure 2:
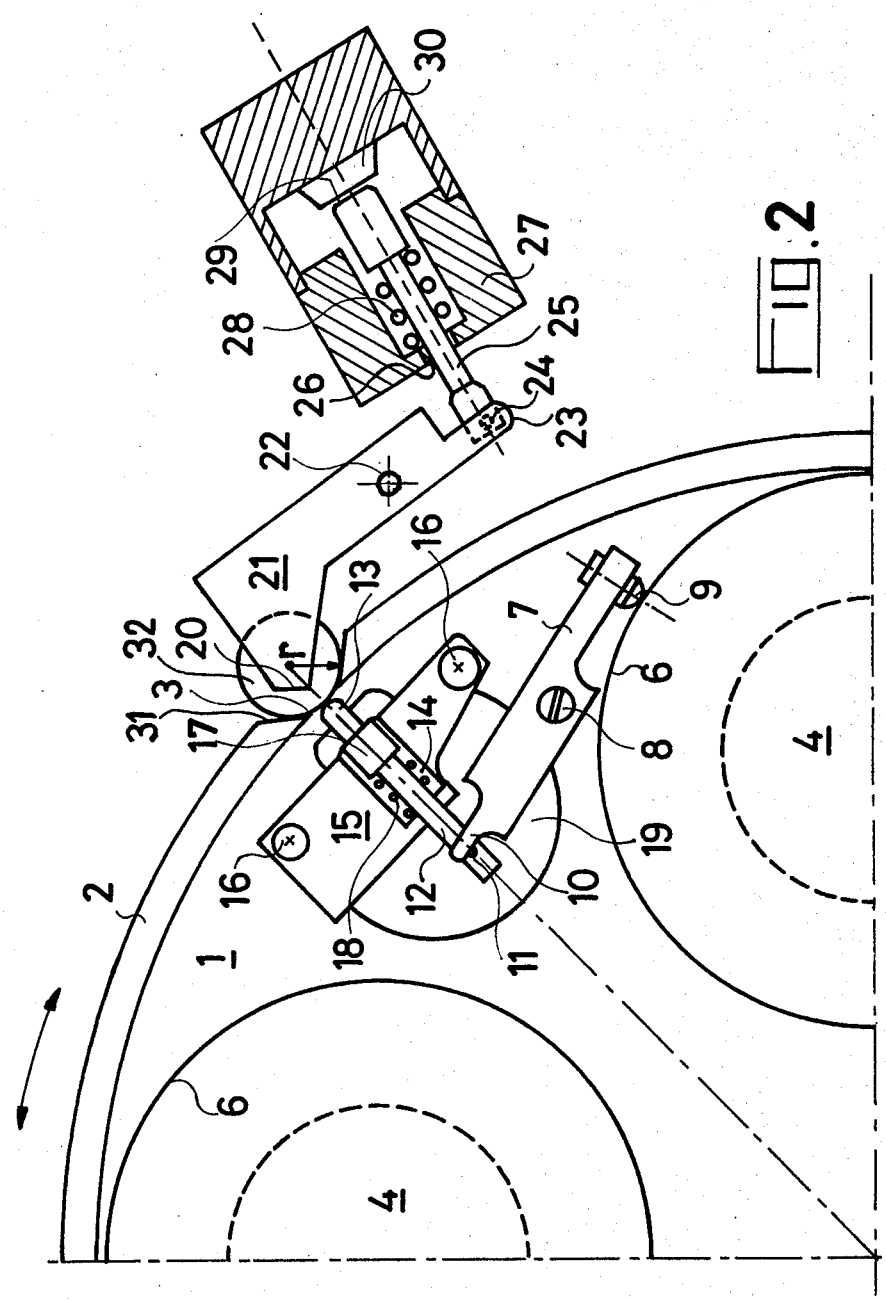
FIG. 2 illustrates a detail of an example of a device in accordance with the invention.

A safety system for monitoring the presence and appropriate positioning of the detachable elements 6 in their locations 4 is associated with each of the locations. This system, shown in FIG. 2, comprises an arm 7, capable of motion about a first fixed pivot 8, provided at one of its ends with a follower 9 which is arranged to come into contact with the periphery of the corresponding detachable element 6, and at its other end with a bracket 10 resting upon a pin 11 arranged at one of the ends of a first rod 12, the other end of which carries on obturating stud 13. The rod 12 can slide in a cylinder 14 formed in a component 15 attached to the mounting plate 1 by means of screws 16, for example. A recess 19 in the mounting plate 1 accommodates the body of the cylinder 14. The rod 12 comprises a collar 17 by which it is guided in cylinder 14. A spring 18 arranged around rod 12, beneath collar 17, is arranged to urge the obturating stud 13 into the corresponding slot 3 when detachable element 6 has not been placed in the location 4 provided therefor.

In operation, the mounting plate 1 can rotate about its own axis under the control of a motor and reduction gear set (not shown in the figure). A set of gears (not shown) enables the mounting plate 1 to perform a small displacement to either side of the selected position, corresponding to the utilization of a given detachable element 6. When the detachable element 6 is placed in position, the follower 9 comes into contact with the wall forming the periphery of this element 6, with the result that the obturating-stud 13 is withdrawn from the slot 3. With its obturating-stud 13 now retracted, the slot 3 is positioned opposite a locking index 20 forming part of a safety system.

This safety system comprises a lever 21 pivoting about a pin 22 and equipped, at one of its ends, with index 20 and, at the other, with a bracket 23 itself pivoting about a pin 24 fixed to a second rod 25 which can slide in the opening 26 formed in a body 27. A bias spring 28 is arranged around the rod 25 to keep the index 20 in contact with the peripheral part of the rim 2 of the mounting plate 1.

In operation, when the selected slot 3 of the mounting plate 1 is arranged opposite index 20, the latter moves into slot 3 if its obturating-stud 13 has been retracted, if the corresponding detachable element 6 is arranged in its location 4. The lever 21 pivots about its pin 22 imparting to the rod 25 a translatory motion which can be utilized to make a contact or to actuate a relay. In the example shown in FIG. 2, the end 29 of the rod 25 operates a safety electrical switch 30 which can supply voltage to a microwave generator and the associated particle accelerator, furnishing an irradiating beam in the trajectory of which the preselected detachable element 6 is arranged.

In order to achieve more accurate positioning of the mounting plate 1, that is to say of the preselected slot 3, in relation to the locking index 20, the latter can be equipped at its tip with a roller 32 of radius $r$. The slot 3 can take the shape of a V, open towards the exterior of the mounting plate, so that the roller 32 accurately locates in the flare 31 of the slot 3 due to the small displacement of the mounting plate 1 to either side of the selected position.

Figure 3:
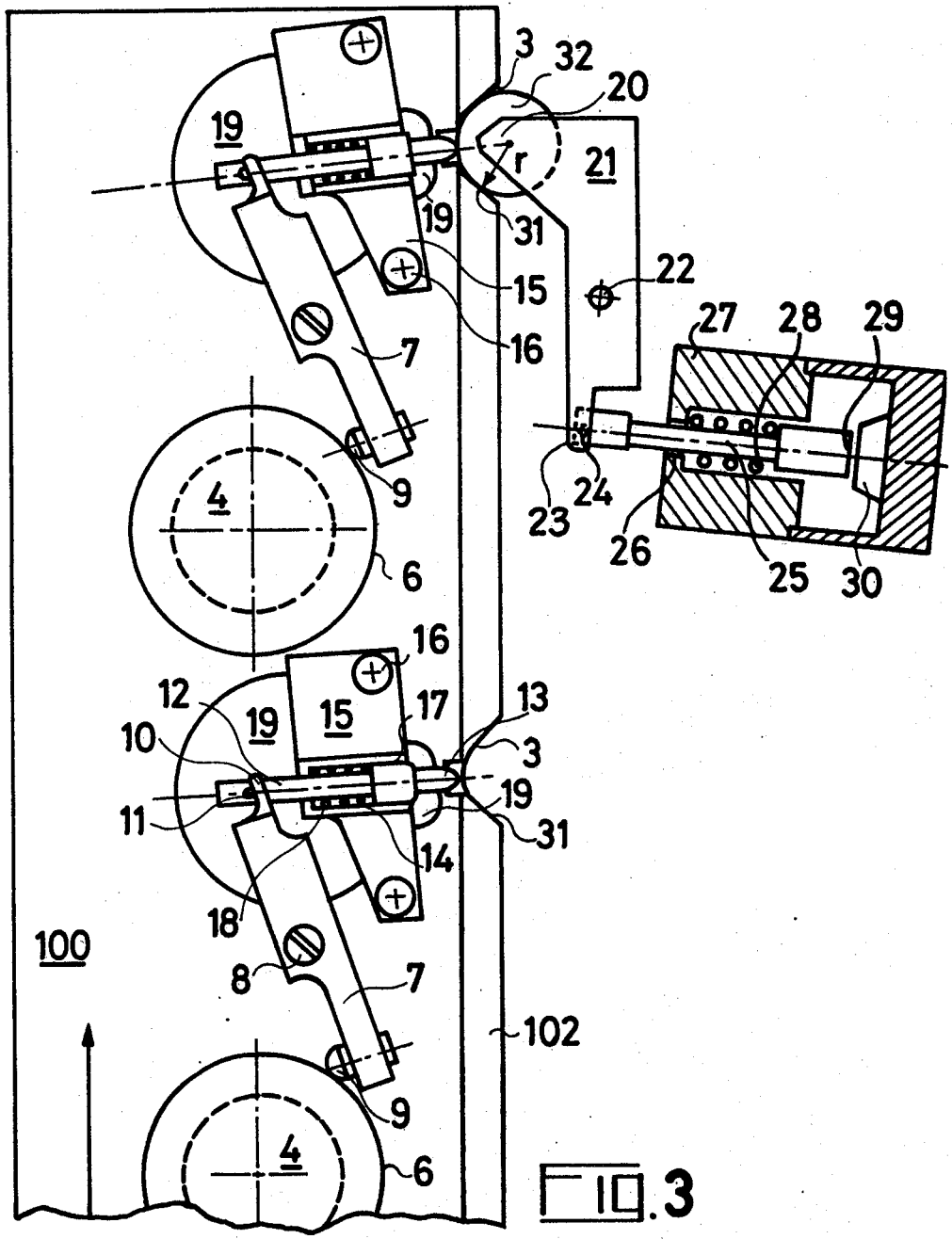
FIG. 3 illustrates another example of a device in accordance with the invention.

In another embodiment, illustrated in FIG. 3, the device in accordance with the invention comprises a rectangular mounting plate 100 which displaces longitudinally. Associated with this supporting plate 100 there is a system for monitoring the positioning of the detachable elements 6 in their locations 4, and a safety locking system, both of the aforedescribed kind, similar references corresponding to similar elements. The monitoring device in accordance with the invention can be utilized to monitor the placing in position of targets or filters of detachable design, which are to be successively placed in the path of the irradiating beam of a radiotherapy apparatus.

In order to prevent any confusion between the detachable elements 6 at the time at which they are placed in position in the supporting plate, these elements can be equipped with mechanical positioning keys or have different dimensions.

Finally, if the mounting plate 1 performs combined motions (rotation about an axis and translation along the axis), the locking index is arranged to displace along an axis perpendicular to the mounting plate 1 in order to remain in the plane of the latter.

What I claim is:

1. A device for monitoring the positioning of detachable elements in their mountings comprising
   a mounting plate with $n$ openings known as "locations", designed to receive said detachable elements,
   said mounting plate being provided at its periphery with a thick rim provided with $n$ slots and a safety system for monitoring the positioning of said elements, said safety system comprising $n$ obturating-studs associated with said $n$ slots;
   means being provided to enable each of said obturating-studs to be retracted from its slot when the detachable element is appropriately positioned in its corresponding location;
   said mounting plate being immobilizable in a given position by means of a safety locking system comprising an index which can be introduced into said slot corresponding to the selected location, after the retraction of said obturating-stud from said slot when said selected location is equipped with its detachable element;
   means being provided for positioning said selected slot opposite said index, and said index actuating a safety electrical switch.

2. A device as claimed in claim 1, wherein said index is maintained in contact with the rim of said mounting plate by means of a return spring which ensures the introduction of said index into said selected slot when said obturating-stud is withdrawn from said selected slot, said selected slot being located opposite said index.

3. A device as claimed in claim 1, wherein said selected slot has the shape of a V, flaring towards the exterior of the mounting plate.

4. A device as claimed in claim 3, wherein said index is provided at its tip with a roller of radius $r$ designed to locate in the flared part of said selected slot.

5. A device as claimed in claim 1, comprising a lever designed to pivot about a fixed pivot, said index being arranged at one end of said lever, the other end of said lever being secured to a rod enable to actuate a safety electrical switch when said index penetrates into said selected slot disposed opposite it.

6. A device as claimed in claim 1, wherein said mounting plate is made of metal and is circular in shape; said circular mounting plate being provided with means enabling it to rotate about an axis perpendicular to it, at its center, and said locations being distributed in the peripheral zone of said circular supporting plate; each location being associated with a follower mechanically linked to one of said obturating-studs, said follower bearing against the periphery of said detachable element when arranged in its corresponding location.

7. A device as claimed in claim 1, wherein said mounting plate is made of metal and is rectangular in shape, means being provided which enable said mounting plate to perform a longitudinal displacement, said locations being distributed longitudinally on said mounting plate, and each location being associated with a follower linked mechanically to one obturating-stud, said follower bearing against the edge of said detachable element when arranged in its corresponding location.

8. A device as claimed in claim 1, wherein said mounting plate is associated with means for performing combined motions of rotation of said mounting plate about an axis perpendicular to it at its center, and of translation along said axis, said locking index being arranged to perform a translatory motion identical to that of said mounting plate, in a direction parallel to said axis, and to remain in the plane of said mounting plate.

9. A device as claimed in claim 1, wherein said detachable elements and the corresponding locations are equipped with mechanical positioning keys.

10. A device as claimed in claim 1, wherein said detachable elements have different dimensions, and said locations have dimensions corresponding to said dimensions of the associated detachable elements.

* * * * *